United States Patent [19]
Grandy et al.

[11] Patent Number: 5,821,067
[45] Date of Patent: Oct. 13, 1998

[54] MAMMALIAN METHADONE-SPECIFIC OPIOID RECEPTOR AND USES IN BINDING ASSAYS

[75] Inventors: David K. Grandy; James R. Bunzow, both of Portland, Oreg.; Olivier Civelli, Aesch, Switzerland

[73] Assignee: State of Oregon, Portland, Oreg.

[21] Appl. No.: 911,245

[22] Filed: Aug. 15, 1997

Related U.S. Application Data

[62] Division of Ser. No. 149,093, Nov. 8, 1993, Pat. No. 5,658,783.

[51] Int. Cl.$^6$ ............................. C12Q 1/02; C07K 14/705
[52] U.S. Cl. .................. 435/7.2; 435/7.21; 435/69.1; 435/252.3; 435/254.11; 435/320.1; 435/325; 530/350
[58] Field of Search .................... 435/7.2, 69.1, 435/325, 252.3, 254.11, 320.1, 7.21; 530/350

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Nilsen et al. | 435/91 |

OTHER PUBLICATIONS

Gluzman et al., (1981) *Cell*, 23:175–182.
Walters, (1993) "Computer–Assisted Modeling of Drugs." *Pharmaceutical Biotechnology*, pp. 165–174.
Thomas & Capecchi, (1987) *Cell*, 51: 503–512.
Bertling, (1987) *Bioscience Reports*, 7: 107–112.
Smithies et al., (1985) *Nature*, 317: 230–234.
Kieffer et al., (1992) *Proc. Natl. Acad. Sci.*, 89: 12048–12052.
Evans et al., (1992) *Science*, 258: 1952–1955.
Chirgwin et al., (1979) *Biochemistry*, 18: 5294–5299.
Saiki et al., (1988) *Science*, 239: 487–491.
Sanger et al., (1977) *Proc. Natl. Acad. Sci.*, 74: 5463–5467.
Eisenberg et al., (1984) *J. Molec. Biol.*, 179: 125–142.
Chen & Okayama, (1987) *Molec. Cell. Biol.*, 7: 2745–2752.
Bunzow et al., (1988) *Nature*, 336: 783–787.
Arizza et al., (1988) *Neuron*, 1: 887–900.
Blakely et al., (1991) *Anal. Biochem.*, 194: 302–308.
Felgner et al., (1987) *Proc. Natl. Acad. Sci.* 84: 7413–7417.
Arizza et al., (1992) *J. Neurosci.*, 12: 4045–4055.
Smith & Johnson, (1988) *Gene*, 67: 31–40.
Chen et al., (1993) "Molecular Cloning and Functional Expression of a ν–Opioid Receptor from Rat Brain." *Molec. Pharmacol.* 44: 8–12—P.

Yasuda et al., (1993) "Cloning and functional comparison of κ and δ opioid receptors from mouse brain." *Proc. Natl. Acad. Sci.*, 90: 6736–6740.
Bzdega et al., (1993) "Regional expression and chromosomal location of the δ opiate receptor gene.", *Proc. Natl. Acad. Sci.*, 90:9305–9309.
Brownstein et al., (1993) "A brief history of opiates, opioid peptides amid opioid receptors." *Proc. Natl. Acad. Sci.*, 90: 5391–5393.
DiChara & North, (1992) "Neurobiology of opitate abuse." *Trends in Phamacol. Sci.*, 13:185–193.
Maneckji and Minna, (1992) "Nonconventional opioid binding sites mediate growth inhibijtory effects of methadone on human lung cancer cells." *Proc. Natl. Acad. Sci.*, 89: 1169–1173.
McKnight & Rees, (1991) "Opioid Receptors and their Ligands." *Neurotransmissions*, 7: 1–6.
Goldstein, (1987) "Binding selectivity profiles for ligands of multipe receptor types: focus on opiod receptors." *Trends in Pharmacol. Sci.*, 8: 456–459.
Kristensen et al., (1995) *Life Sciences*, vol. 56, p. 56.
Fukuda et al., (1993) *FEBS Letters*, vol. 327, p. 311.
Wang et al., (1993) *PNAS*, vol. 90, p. 10230.
Reeck et al., (1987) *Cell*, vol. 50, p. 667.
Lewin, (1987) *Science*, vol. 23.

*Primary Examiner*—Sally Teng
*Attorney, Agent, or Firm*—McDonnell Boehnen Hulbert & Berghoff

[57] ABSTRACT

The present invention relates to a novel mammalian met one-specific opioid receptor protein and genes that encode a such protein. The invention is directed toward the isolation, characterization and pharmacological use of mammalian methadone-specific opioid receptor proteins. The invention specifically provides isolated complementary DNA copies of mRNA corresponding to the rat homologue or the mammalian methadone-specific opioid receptor gene. Also provided are recombinant expression constructs capable of expressing the mammalian methadone-specific opioid receptor genes of the invention in cultures of transformed prokaryotic and eukaryotic cells, as well as such cultures of transformed cells that synthesize the mammalian methadone-specific opioid receptor proteins encoded therein. The invention also provides methods for screening compounds in vitro that are capable of binding to the mammalian methadone-specific opioid receptor proteins of the invention, and further characterizing the binding properties of such compounds in comparison with known opioid receptor agonists and antagonists.

10 Claims, 10 Drawing Sheets

FIG. 1A

```
CCGAGGAGCCATTCCCAGCCGCAGCAGACCCCAATCTAGAGTGAGAGTCATTGCTCAGTCCACTGTGCTCC        71
TGCCTGCCCGCCTTTCTGCTAAGCATTGGGGTCTATTTTGCGCCCAGCTTCTGAAGAGGCTGTGTGTGCCG        142

TTGGAGGAACTGTACTGAGTGGCTTTGCAGGGTGACAGCATGGAGTCCCTCTTTCCTGCTCCATACTGGGAG        214
                                      M  E  S  L  F  P  A  P  Y  W  E

GTCTTGCATGGCAGCCACTTTCAAGGGAACCTGTCCCTCCTAAATGAGACCGTACCCCACCACCTGCTCCTC        286
 V  L  H  G  S  H  F  Q  G  N  L  S  L  L  N  E  T  V  P  H  H  L  L
                      A              A

AATGCTAGTCACAGCGCCTTCCTGCCCCTTGGACTCAAGGTCACCATCGTGGGGCTCATCTTGGCTGTGTGC       358
 N  A  S  H  S  A  F  L  P  L G L K V T I V G L I L A V C
 A                              I

ATCGGGGGCTCCTGGGGAACTGCCTCGTCATGTATGTCATCCTCAGGACACCCAAGATGAAGACAGCTACC        430
 I G G L L G N C L V M Y V I L   R  T  P  K  M  K  T  A  T
         I                                                II

AACATTTACATATTTAATCTGGCACTGGCTGATACCCTGGTCTTGCTAACACTGCCCTTCCAGGGCACAGAC      502
 N I Y I F N L A L A D T L V L L T L P F Q G T  D
                II

ATCCTACTGGGCTTCTGGCCATTTGGGAAAGCACTCTGCAAGACTGTCATTGCTATCGACTACTACAACATG      574
 I  L  L  G  F  W  P  F  G  K  A  L  C  E  T V I A I D Y Y N M
                                                III

TTTACCAGCACTTTTACTCTGACCGCCATGAGCGTAGACCGCTATGTGGCTATCTGCCACCCTATCCGTGCC      646
 F T S T F T L T A M S V  D  R  Y  V  A  I  C  H  P  I  R  A
       III
```

FIG. 1B

```
CTTGATGTTCGGACATCCAGCAAAGCCCAGGCTGTTAATGTGGCCATATGGGCCCTGGCTTCAGTGGTTGGT    718
 L  D  V  R  T  S  S  K  A  Q  A  V  N  V  A  I  M  A  L  A  S  V  V  G
                   *                              IV

GTTCCTGTTGCCATCATGGGTTCAGCACAAGTGGAAGATGAAGAGATCGAGTGCCTGGTGGAGATCCCTGCC    790
 V  P  V  A  I  M  G  S  A  Q  V  E  D  E  E  I  E  C  L  V  E  I  P  A
             IV

CCTCAGGACTATTGGGGCCCTGTATTCGCCATCTGCATCTTCCTTTTTTCCTTCATCATCCCTGTGCTGATC    862
 P  Q  D  Y  W  G  P  V  F  A  I  C  I  F  L  F  S  F  I  I  P  V  L  I
                                            V

ATCTCTGTCTGCTACAGCCTCATGATTCGACGACTTCGTGGTGTCCGTCTGCTTTCAGGCTCCCGGGAGAAG    934
 I  S  V  C  Y  S  L  M  I  R  R  L  R  G  V  R  L  L  S  G  S  R  E  K
          V

GACCGAAACCTGCGGCGTATCACTCGACTGGTGCTGGTAGTGGTGGCTGTGTTTGTGGGCTGCTGGACGCCT    1006
 D  R  N  L  R  R  I  T  R  L  V  L  V  V  V  A  V  F  V  G  C  W  T  P
                               VI

GTGCAGGTGTTTGTCCTGGTTCAAGGACTGGGTGTTCAGCCAGGTAGTGAGACTGCAGTTGCCATCCTGCGC    1078
 V  Q  V  F  V  L  V  Q  G  L  G  V  Q  P  G  S  E  T  A  V  A  I  L  R
       VI

TTCTGCACAGCCCTGGGCTATGTCAACAGTTGTCTAATCCCATTCTCTATGCTTTCCTGGATGAGAACTTC    1150
 F  C  T  A  L  G  Y  V  N  S  C  L  I  P  F  L  Y  A  F  L  D  E  N  F
              VII
```

FIG. 1C

```
AAGGCCTGCTTTAGAAAGTTCTGCTGTGCTTCATCCCTGCACCGGGAGATGCAGGTTTCTGATCGTGTGCGG
 K  A  C  F  R  K  F  C  C  A  S  S  L  H  R  E  M  Q  V  S  D  R  V  R
                                                              *
ACGATTGCCAAGGATGTTGGCCTTGGTTGCAAGACTTCTGAGACAGTACCACGGCCAGCATGACTAGGCGTG
 T  I  A  K  D  V  G  L  G  C  K  T  S  E  T  V  P  R  P  A

GACCTGCCCATGGTGCCTGTCAGCCCACAGAGCCCATCCTACACCCAACACGGAGCTCACACAGGTCACTGC
TCTCTAGGTTGACCCTGAACCCTTGAGAGCATCTGAGCCCTTGAATGGCTTTTCTTTTGGATCAGGATGCTCAGT
CCTAGAGGAAGACC
```

```
LC132                   MESLFPAPYWEVL
Rat µ-Opioid Receptor   MDSSTGPGNTSDCSDPLAQASCSPAPGSWLNLS
Mouse δ-Opioid Receptor                       MELVPSARAELQSS
Mouse κ-Opioid Receptor           MESPIQIFRGDPGPTCSPSACLLP I
LC132    HGSHFEQGNLSLLNETVPHHLLLNASHSAFLPLGLKVTIVGLILAVCIGGLLGNCL
(µ-OR)   HVDGNQSDPCGLNRTGLGGNDSLCPQTGSPSMVTAITIMALYSIVCVVGLFGNFL
(δ-OR)   PLVNLSDAFPSAGANASGSPGARSASSLALAIAITALYSAVCAVGLLGNVL
(κ-OR)   NSSSWFPNWAESDSNGSVGSEDQQLESAHISPAIPVIITAVYSVVFVVGLVGNSL II
LC132    VMYVILRTPKMKTATNIYIFNLALADTLVLLTLPFQGTDILLGFWPFGKALCKTV
(µ-OR)   VMYVIVRYTKMKTATNIYIFNLALADALATSTLPFQSVNYLMGTWPFGTILCKIV
(δ-OR)   VMFGIVRYTKLKTATNIYIFNLALADALATSTLPFQSAKYLMETWPFGELLCKAV
(κ-OR)   VMFVIIRYTKMKTATNIYIFNLALADALVTTMPFQSAVYLMNSWPFGDVLCKIV III                                   IV
LC132    IAIDYYNMFTSTFTLTTAMSVDRYVAICHPIRALDVRTSSKAQAVNVAIWALASVV
(µ-OR)   ISIDYYNMFTSIFTLCTMSVDRYIAVCHPVKALDFRTPRNAKIVMVCNWILSSAI
(δ-OR)   LSIDYYNMFTSIFTLTMMSVDRYIAVCHPVKALDFRTPAKAKLIMICIWVLASGV
(κ-OR)   ISIDYYNMFTSIFTLTMMSVDRYIAVCHPVKALDFRTPLKAKIIMICIWLLASSV
```

FIG. 2B

```
                                                                              V
LC132    GVPVAIMGSAQ   VEDEEIECLVEIPAP QDYWGPVFAICIFLFSFIIPVLIISV
(μ-OR)   GLPVMFMATTK   YRQGSIDCTLTFSHP TWYENLLKICVFIFAFIMPILIITV
(δ-OR)   GVPIMVMAVTQ   PRDFAVVCMLQFPSP SWYWDTVTKICVFLFAFVVPILIITV
(κ-OR)   GISAIVLGGTKVREDVDVIECSLQFPDDEYSWWDLFMKICVFVFAFVIPVLIIIV

VI
LC132    CYSLMIRRLRGVRLLSGSREKDRNLRRITRLVLVLVVAVFVGCWTPVQVFVLVQGL
(μ-OR)   CYGLMILRLKSVRMLSGSKKKDRNLRRITRMVLVVVAVFIVCWTPIHIYVIIKAL
(δ-OR)   CYGLMLLRLRSVRLLSGSKKKDRSLRRITRMVLVVVGAFVVCWAPIHIFVIVWTL
(κ-OR)   CYTLMILRLKSVRLLSGSRKKDRNLRRITKLVLVVVAVFIICWTPIHIFILVEAL

VII
LC132    GVQPGSETAVAIL RFCTALGYVHSCLNPILYAFLDENFKACFRKFCCASSLHRE
(μ-OR)   ITIPETTFQTVSW HFCIALGYTMSCLMPVLYAFLDEMFKRCFREFCIPTSSTIE
(δ-OR)   VDINRRDPLVVAALHLCIALGYAMSSLMPVLYAFLDEMFKRCFRQLCRTPCGRQE
(κ-OR)   GSTSHSTAALSSY YFCIALGYTMSSLMPVLYAFLDEMFKRCFRDFCFPIKMRME

LC132    MQVSDRVRTIAKDVGLGCKTSETVPRPA    367
(μ-OR)   QQNSTRVRQNTREHPSTANTVDRTNHQLENLEAETAPLP    398
(δ-OR)   PGSLRRPRQATTRERVTACTPSDGPGGAAA    372
(κ-OR)   RQSTNRVRNTVQDPASMRDVGGMNKPV    380
```

MAMMALIAN METHADONE-SPECIFIC OPIOID RECEPTOR AND USES IN BINDING ASSAYS

This application is a divisional of U.S. Ser. No. 08/149,093, filed Nov. 8, 1993, now U.S. Pat. No. 5,658,783, issued Aug. 19, 1997.

This invention was made with government support under National Institute of Health grants R01 MH48991. The government has certain rights to this invention.

BACKGROUND OF THE INVENTION

1. Field of the Invention

This invention relates to opioid receptors from mammalian species and the genes corresponding to such receptors. Specifically, the invention relates to the isolation, cloning and sequencing of complementary DNA (cDNA) copies of messenger RNA (mRNA) encoding a novel mammalian opioid receptor gene. The invention also relates to the construction of recombinant expression constructs comprising cDNA of this novel opioid receptor gene, said recombinant expression constructs being capable of expressing opioid receptor protein in cultures of transformed prokaryotic and eukaryotic cells. Production of the receptor protein in such cultures is also provided. The invention relates to the use of such cultures of such transformed cells to produce homogeneous compositions of the novel opioid receptor protein. The invention also provides cultures of such cells producing this opioid receptor protein for the characterization of novel and useful drugs. Antibodies against and epitopes of this novel opioid receptor protein are also provided by the invention.

2. Background of the Invention

The use (and abuse) of opiates, archetypally opium and morphine, have been known since antiquity (reviewed in Brownstein, 1993, Proc. Natl. Acad. Sci. USA 90: 5391–5393). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (see DiChara & North, 1992, Trends in Phamacol. Sci. 13: 185–193 for review). Accompanying this finding of an endogenous opiate was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution: these comprise the $\mu$, $\delta$, $\kappa$ and $\sigma$ receptors (the $\sigma$ receptor has been determined to be a non-opioid receptor with cross-reactivity to some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. USA 89: 12048–12052 disclosed the isolation of a cDNA copy of the mouse $\sigma$-opioid receptor by expression cloning.

Evans et al., 1992, Science 258: 1952–1955 disclose the isolation of a cDNA copy of the mouse $\sigma$-opioid receptor by expression cloning.

Chen et al., 1993, Molec. Pharmacol. 44: 8–12 disclose the isolation of a cDNA copy of the rat $\mu$-opioid receptor.

Yasuda et al., 1993, Proc. Natl. Acad. Sci. USA 90: 6736–6740 disclose the isolation of a cDNA copy of each of the mouse $\kappa$- and $\delta$-opioid receptor.

Bzdega et al., 1993, Proc. Natl. Acad. Sci. USA 90: 9305–9309 disclose the isolation and chromosomal location of the $\delta$-opioid receptor in the mouse.

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that hundreds, if not thousands, of chemical compounds must be tested in order to identify a single effective therapeutic agent that does not engender unacceptable levels of undesirable or deleterious side effects. There is an increasing need for economical methods of testing large number of chemical compounds to quickly identify those compounds that are likely to be effective in treating disease.

This is of particular importance for psychoactive and psychotropic drugs, due to their pharmacological importance and their potential to greatly benefit or greatly harm human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human opioid receptor molecules in vitro would provide an efficient and economical means for rational drug design and rapid screening of potentially useful compounds. For these and other reasons, development of in vitro screening methods for psychotropic drugs has numerous advantages and is a major research goal in the pharmaceutical industry.

SUMMARY OF THE INVENTION

The present invention relates to the cloning, expression and functional characterization of a mammalian methadone-specific opioid receptor (MSOR) gene. The invention comprises nucleic acids having a nucleotide sequence of a novel mammalian MSOR gene. The nucleic acids provided by the invention comprise a complementary DNA (cDNA) copy of the corresponding mRNA transcribed in vitro from the MSOR genes of the invention. Also provided are the deduced amino acid sequence of the cognate protein of the cDNA provided by the invention.

This invention provides nucleic acids, nucleic acid hybridization probes, recombinant eukaryotic expression constructs capable of expressing the MSOR receptors of the invention in cultures of transformed cells, such cultures of transformed eukaryotic cells that synthesize the MSOR receptors of the invention, homogeneous compositions of the MSOR receptor protein, and antibodies against and epitopes of the MSOR receptor protein of the invention. Methods for characterizing these receptor proteins and methods for using these proteins in the development of agents having pharmacological uses related to these receptors are also provided by the invention.

In a first aspect, the invention provides a nucleic acid having a nucleotide sequence encoding a mammalian methadone-specific opioid receptor. In a preferred embodiment, the nucleic acid encodes the rat MSOR receptor. In this embodiment of the invention, the nucleotide sequence includes 1452 nucleotides of the rat MSOR cDNA comprising 1101 nucleotides of coding sequence, 181 nucleotides of 5' untranslated sequence and 170 nucleotides of 3' untranslated sequence. In this embodiment of the invention, the nucleotide sequence of the MSOR receptor consists essentially of the nucleotide sequence depicted in FIGS. 1A through 1C (SEQ ID No:3). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding MSOR disclosed herein.

The corresponding MSOR protein molecule, having the deduced amino acid sequence consisting essentially of the sequence shown in FIGS. 1A through 1C (SEQ ID No.:4), is also claimed as an aspect of the invention. The use of the term "consisting essentially of" herein is as described above. Similarly, the MSOR protein molecule, having the deduced amino acid sequence consisting essentially of the sequence shown in FIGS. 1A through 1C (SEQ ID No.:4), is also claimed as an aspect of the invention. MSOR protein molecules provided by the invention are understood to have substantially the same biological properties as the MSOR protein molecule encoded by the nucleotide sequence described herein.

In another aspect, the invention comprises a homogeneous composition of the 47 kD mammalian MSOR transporter or derivative thereof, said size being understood to be the size of the protein before any post-translational modifications thereof. The amino acid sequence of the MSOR transporter or derivative thereof preferably consists essentially of the amino acid sequence of the MSOR transporter protein shown in FIGS. 1A through 1C (SEQ ID No:4).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the MSOR receptor gene in various tissues of mammals, including humans. It is also an object of the present invention to provide nucleic acid hybridization probes derived from the sequences of mammalian MSOR receptor genes of the invention to be used for the detection and diagnosis of genetic diseases. It is an object of this invention to provide nucleic acid hybridization probes derived from the DNA sequences of the mammalian MSOR receptor genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of MSOR receptor-specific antibodies, or useful as competitors of MSOR receptor molecules for agonist, antagonist or drug binding, or to be used for the production of inhibitors of the binding of agonists or antagonists or analogues thereof to such MSOR receptor molecules.

The present invention also provides antibodies against and epitopes of the mammalian MSOR receptor molecules of the invention. It is an object of the present invention to provide antibodies that are immunologically reactive to the MSOR receptors of the invention. It is a particular object to provide monoclonal antibodies against these MSOR receptors. Hybridoma cell lines producing such antibodies are also objects of the invention. It is envisioned that such hybridoma cell lines may be produced as the result of fusion between a non-immunoglobulin producing mouse myeloma cell line and spleen cells derived from a mouse immunized with a cell line which expresses antigens or epitopes of a mammalian MSOR receptor of the invention.

The present invention also provides hybridoma cell lines that produce such antibodies, and can be injected into a living mouse to provide an ascites fluid from the mouse that is comprised of such antibodies. It is a further object of the invention to provide immunologically-active epitopes of the mammalian MSOR receptor proteins of the invention. Chimeric antibodies immunologically reactive against the MSOR receptor proteins of the invention are also within the scope of this invention.

The present invention provides recombinant expression constructs comprising a nucleic acid encoding a mammalian MSOR receptor of the invention wherein the construct is capable of expressing the encoded MSOR receptor in cultures of cells transformed with the construct.

Preferred embodiments of such constructs comprise the MSOR receptor cDNA depicted in FIGS. 1A through 1C (SEQ ID No.:3), such constructs being capable of expressing the MSOR receptor encoded therein in cells transformed with the construct.

The invention also provides cultures cells transformed with the recombinant expression constructs of the invention, each such culture being capable of and in fact expressing the mammalian MSOR receptor encoded in the transforming construct.

The present invention also includes within its scope protein preparations of prokaryotic and eukaryotic cell membranes containing the MSOR receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian MSOR receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects.

The present invention is also useful for the detection of analogues, agonists or antagonists, known or unknown, of the mammalian MSOR receptors of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A–1C illustrates the nucleotide (SEQ ID No.:3) and amino acid (SEQ ID No.:4) sequences of the rat methadone-specific opioid receptor.

FIGS. 2A and 2B presents an amino acid sequence comparison between the rat methadone-specific 5 opioid receptor protein (LC132, SEQ ID NO.:4) and the rat $\mu$-opioid receptor (SEQ ID NO.:5), and the mouse δ- and κ-opioid receptor proteins.

DETAILED DESCRIPTION OF THE PREFERRED EMBODIMENTS

Figure 3A:
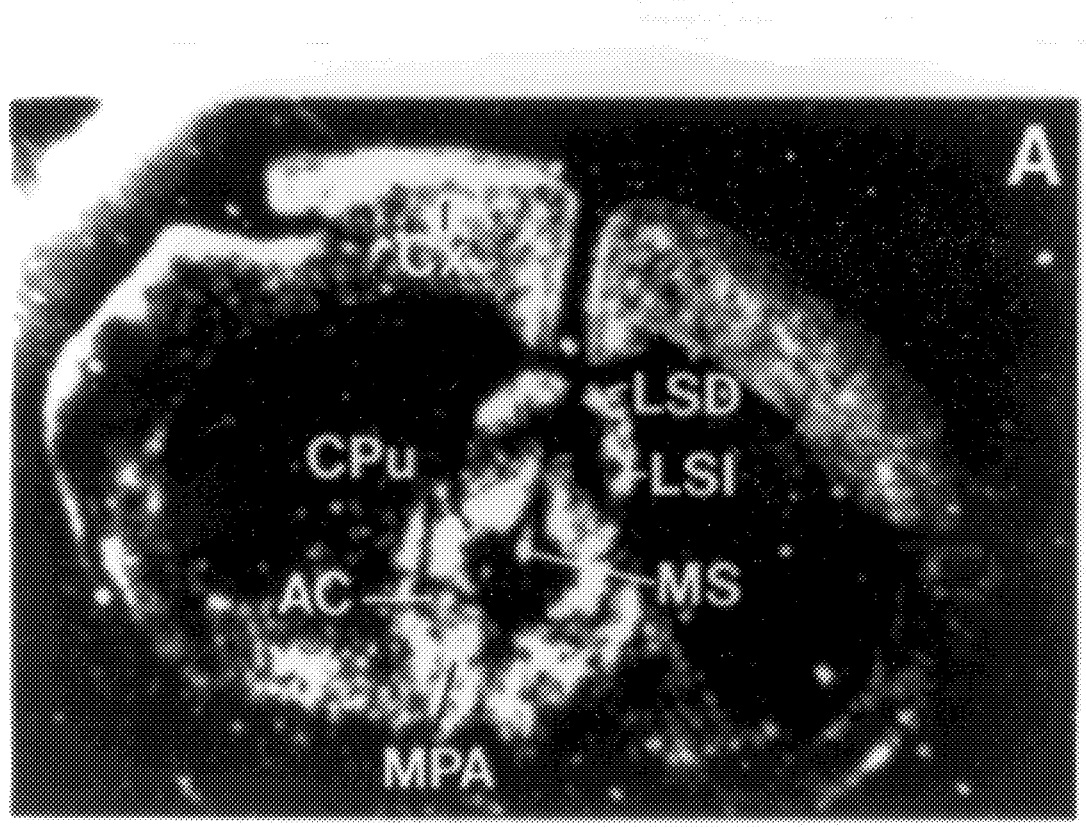
FIG. 3A–3C illustrates in situ hybridization of rat brain sections with a nucleic acid hybridization probe specific for the methadone-specific mammalian opioid receptor of the invention.

The term "mammalian methadone-specific opioid receptor (MSOR)" as used herein refers to proteins consisting essentially of, and having substantially the same biological activity as, the protein encoded by the nucleic acid depicted in FIGS. 1A through 1C (SEQ ID No.:3). This definition is intended to encompass natural allelic variations in the disclosed MSOR sequence. Cloned nucleic acid provided by the present invention may encode MSOR protein of any species of origin, including, for example, mouse, rat, rabbit, cat, and human, but preferably the nucleic acid provided by the invention encodes MSOR receptors of mammalian, most preferably rat and human, origin.

The nucleic acid hybridization probes provided by the invention comprise DNA or RNA consisting essentially of the nucleotide sequence of the MSOR receptor, depicted in FIGS. 1A through 1C (SEQ ID No.:3), or any portion thereof effective in nucleic acid hybridization. Mixtures of such nucleic acid hybridization probes are also within the scope of this embodiment of the invention. Nucleic acid probes as provided herein are useful for detecting MSOR receptor gene expression in cells and tissues using techniques well-known in the art, including but not limited to Northern blot hybridization, in situ hybridization and Southern hybridization to reverse transcriptase-polymerase chain reaction product DNAs. The probes provided by the present invention, including oligonucleotides probes derived therefrom, are also useful for Southern hybridization of mammalian, preferably human, genomic DNA for screening for restriction fragment length polymorphism (RFLP) associated with certain genetic disorders.

The production of proteins such as the MSOR receptor molecule from cloned genes by genetic engineering means is well known in this art. The discussion which follows is accordingly intended as an overview of this field, and is not intended to reflect the full state of the art.

DNA encoding an MSOR receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the MSOR receptor disclosed herein. Probes may be labeled with a detectable group such as a fluorescent group, a radioactive atom or a chemiluminescent group in accordance with known procedures and used in conventional hybridization assays, as described in greater detail in the Examples below. In the alternative, MSOR derived nucleic acid sequences may be obtained by use of the polymerase chain reaction (PCR) procedure, using PCR oligonucleotide primers corresponding to nucleic acid sequence information derived from an MSOR receptor as provided herein. See U.S. Pat. Nos. 4,683,195 to Mullis et al. and 4,683,202 to Mullis.

The MSOR receptor protein may be synthesized in host cells transformed with a recombinant expression construct comprising a nucleic acid encoding the MSOR receptor cDNA. Such recombinant expression constructs can also be comprised of a vector that is a replicable DNA construct. Vectors are used herein either to amplify DNA encoding an MSOR receptor and/or to express DNA encoding an MSOR receptor gene. For the purposes of this invention, a recombinant expression construct is a replicable DNA construct in which a nucleic acid encoding an MSOR receptor is operably linked to suitable control sequences capable of effecting the expression of the MSOR receptor in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is RcRVS (Invitrogen, San Diego, Calif.). Transformed host cells are cells which have been transformed or transfected with recombinant expression constructs made using recombinant DNA techniques and comprising nucleic acid encoding an MSOR protein. Preferred host cells are COS-7 cells (Gluzman, 1981, Cell 23: 175–182) and Ltk⁻ cells. Transformed host cells may express the MSOR receptor protein, but host cells transformed for purposes of cloning or amplifying nucleic acid hybridization probe DNA need not express the receptor. When expressed, the MSOR receptor of the invention will typically be located in the host cell membrane. See, Sambrook et al., ibid.

Cultures of cells derived from multicellular organisms are a desirable host for recombinant MSOR receptor protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture,* Academic Press, Kruse & Patterson, editors (1973). Examples of useful host cell lines are human 293 cells, VERO and HeLa cells, Chinese hamster ovary (CHO) cell lines, mouse Ltk⁻ cell lines and WI138, BHK, COS-7, CV, and MDCK cell lines. COS-7 cells and Ltk⁻ cells are preferred.

The invention provides homogeneous compositions of mammalian methadone-specific opioid receptor protein produced by transformed eukaryotic cells as provided herein. Each such homogeneous composition is intended to be comprised of the MSOR receptor protein that comprises at least 90% of the protein in such a homogenous composition. The invention also provides membrane preparations from cells expressing the MSOR receptor protein as the result of transformation with a recombinant expression construct, as described herein.

Mammalian methadone-specific opioid receptor proteins made from cloned genes in accordance with the present invention may be used for screening opioid analogues, or agonists or antagonists of opioid binding, or for determining the amount of such agonists or antagonists present in a solution of interest (e.g., blood plasma, cerebrospinal fluid or serum). For example, host cells may be transformed with a recombinant expression construct of the present invention, a mammalian MSOR receptor expressed in those host cells, and the cells or membranes thereof used to screen compounds for their effect on opioid agonist binding activity.

By selection of host cells that do not ordinarily express a MSOR receptor, pure preparations of membranes containing the transporter can be obtained.

The recombinant expression constructs of the present invention are useful in molecular biology to transform cells which do not ordinarily express an MSOR receptor to thereafter express this receptor. Such cells are useful as intermediates for making cell membrane preparations useful for receptor binding activity assays, which are in turn useful for drug screening. The recombinant expression constructs of the present invention thus provide a method for screening potentially useful drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful in molecular biology to detect, isolate, characterize and identify novel endogenous opioid receptor agonists and antagonists found in plasma, serum, lymph, cerebrospinal fluid, seminal fluid, or other potential sources of such compounds. This utility thereby enables rational drug design of novel therapeutically-active drugs using currently-available techniques (see Walters, "Computer-Assisted Modeling of Drugs", in Klegerman & Groves, eds., 1993, *Pharmaceutical Biotechnology,* Interpharm Press-:Buffalo Grove, Ill., pp. 165–174).

The recombinant expression constructs of the present invention may also be useful in gene therapy. Cloned genes of the present invention, or fragments thereof, may also be used in gene therapy carried out using homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing MSOR receptor gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding MSOR receptor gene, and potential pathological conditions related thereto.

The invention also provides antibodies that are immunologically reactive to the MSOR receptor protein or epitopes thereof provided by the invention. The antibodies provided by the invention may be raised, using methods well known in the art, in animals by inoculation with cells that express an MSOR receptor or epitopes thereof, cell membranes from such cells, whether crude membrane preparations or membranes purified using methods well known in the art, or purified preparations of proteins, including fusion proteins, particularly fusion proteins comprising epitopes of the MSOR receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the MSOR receptor provided by the invention, or any cell or cell line that expresses the MSOR receptor of the invention, or any epitope thereof, as a result of molecular or genetic engineering, or that has been treated to increase the expression of an endogenous or heterologous MSOR receptor protein by physical, biochemical or genetic means. Preferred cells are *E. coli* and insect SF9 cells, most preferably *E. coli* cells, that have been transformed with a recombinant expression construct of the invention encoding an MSOR receptor protein, and that express the receptor therefrom.

The present invention also provides monoclonal antibodies that are immunologically reactive with an epitope derived from an MSOR receptor of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an MSOR receptor of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an MSOR receptor, made by methods known to those of skill in the art.

The present invention also encompasses an epitope of an MSOR receptor of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an MSOR receptor-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Mammalian Opioid Receptor Probe by Random PCR Amplirication of Rat Brain-derived cDNA Using Degenerate Olieonucleotide Primers In order to clone novel mammalian G-protein coupled receptors, cDNA prepared from RNA from different regions of rat brain was used as template for a polymerase chain reaction (PCR)-based random cloning experiment. PCR was performed using a pair of degenerate oligonucleotide primers corresponding to the putative third and seventh transmembrane regions of a mouse δ-opioid receptor (Kieffer et al., 1992, Proc. Natl. Acad. Sci. USA 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as follows. Total RNA was isolated from various rat brain regions by the guanidinium thiocyanate method (Chirgwin et al., 1979, Biochemistry 18: 5294–5299). First-strand cDNA was prepared from rat brain RNA using standard techniques (see Sambrook et al., 1990, *Molecular Cloning: A Laboratory Manual,* Cold Spring Harbor Press, Cold Spring Harbor Laboratory, N.Y.) using murine reverse transcriptase (BRL, Gaithersburg, Md.) and oligo-dT priming (Sambrook et al., ibid.). The rat brain cDNA preparation was then subjected to 35 cycles of PCR amplification using 500 picomoles of degenerate oligonucleotide primers having the following sequence:

Primer III (sense):
ATGAATTCAC(G/A/C/T)(A/G)T(G/C)ATGAG(C/T)GT(G/C)GAC(C/A)G(C/A)TA
(SEQ ID NO:1)

and

Primer VII (antisense):
TTGTCGAC(G/A)TA(G/A)AG(A/G)A(T/C)(G/A/C/T)GG(G/A)TT
(SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). Each PCR amplification cycle consisted of incubations at 94° C. for 1 min (denaturation), 50° C. for 1.5 min (annealing), and 72° C. for 1.5 min (extension).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a ($^{32}$P)-dCTP-labeled radioactive nucleic acid probe comprising a full-length mouse δ-opioid receptor cDNA at a concentration of 1×10$^6$ cpm/mL under low stringency hybridization conditions (35% formamide, 5X standard citrate saline (SSC; wherein 1X SSC is 0.15M NaCl/0.015M sodium citrate, pH 7.0), 5X Denhardt's solution (wherein 1X Denhardt's solution is 0.02 g/mL each of bovine serum albumin, Ficoll and polyvinylpyrrolidone) at 37° C. overnight. After hybridization, the filters were washed in a solution of 2X SSC/0.1% sodium dodecyl sulfate (SDS) at 55° C. and then exposed to X-ray film (XAR-5, Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. USA 74: 5463–5467) using Sequenase® (U.S. Biochemical Corp., Cleveland, Ohio).

EXAMPLE 2

Isolation of a Novel Mammalian Opioid Receptor cDNA

One of the PCR products (termed LC132) was isolated and sequenced in this way and was found to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)-primed rat brain cDNA. Plaque-containing nitrocellulose filters were hybridized with a ($^{32}$P)-dCTP-labeled, randomly-primed hybridization probe consisting of a fragment of the LC132 PCR product under high stringency conditions (which were identical to the low stringency conditions described above except that the hybridization solution was 50% formamide and hybridized filters were washed at 0.5X SSC/0.1% SDS). Positively-hybridizing λgt11 clones were plaque purified (i.e., grown, replated and re-infected in bacteria until all phage plaques hybridized to the probe, indicating that all plaques arose from phage containing the same insert; see Sambrook et al., ibid.) and analyzed by restriction enzyme digestion. An open reading frame was found on a 3.1 kilobase (kb) EcoRI-digested DNA fragment and was analyzed as follows.

Nucleotide sequence analysis performed essentially as described in Example 1 revealed the sequence shown in FIGS. 1A through 1C (SEQ ID No.: 3). The putative protein product of the gene is also shown in FIG. 1A through 1C (SEQ ID No:4). The sequence was found to have an open reading frame comprising 1101 nucleotides encoding a protein 367 amino acids in length, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains (using the algorithm of Eisenberg et al. (1984, J. Molec. Biol. 179: 125–142)) are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic acid was determined to be a novel mammalian opioid receptor. Comparison of the amino acid sequence of the novel receptor with the amino acid sequences of other known mammalian opioid receptors supported this conclusion.

The predicted amino acid sequences of this novel opioid receptor, the rat μ-opioid receptor (Chen et al., ibid.), the mouse δ-opioid receptor (Evans et al., ibid. and Kieffer et al., ibid.) and the mouse κ-opioid receptor (Yasuda et al., ibid.) are aligned in FIGS. 2A and 2B. Overbars indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. A more detailed comparison of these amino acid sequences are quantified in Table I, showing the percentage extent of homology in pairwise fashion between the different opioid receptors. Comparisons are made individually at each transmembrane domain (TMI-TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is an opioid receptor.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk$^-$ cells (for stable expression assays), and cell membranes (COS-7) or cell lines (Ltk$^-$) were generated that expressed the receptor protein in cellular membranes at the cell surface. Such cells and membranes isolated from such cells were used for biochemical characterization experiments described below.

The entire coding region of the receptor cDNA insert was amplified using PCR as described above with primers specific for sequences FIGS. 1A–1C in the 5' and 3' untranslated sequences; such PCR primers advantageously contained restriction enzyme digestion recognition sites at the 5' termini such that digestion with said restriction enzymes allowed facile cloning of the receptor cDNA into the mammalian expression construct RcRSV (Invitrogen, San Diego, Calif.). PCR products generated into this way were subcloned in to the RcRSV vector using conventional techniques (see Sambrook et al., ibid.) and the orientation of the inserted cDNA confirmed by restriction enzyme digestion analysis of insert-containing subclones. Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. Such membranes were harvested from cells grown on 15 cm plates by pelleting the cells at 20,000 rpm in a solution of 50 mM Tris-HCl (pH 7.4). The protein concentration was adjusted to 15–80 μg/sample for each of the binding studies described below.

These recombinant expression constructs were also introduced into Ltk$^-$ cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. (1988, Nature D: 783–787). In binding experiments, increasing amounts of membrane protein (from 15–80 µg) were incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): ($^3$H)-Tyr-DAla-Gly-Met-Phe-Gly-ol (DAMGO; µ-opioid receptor agonist), [$^3$H]-c[D-penicillamine$^2$, D-penicillamine$^5$]enkephalin (DPDPE; δ agonist), ($^3$H)-U-69,593 (κ agonist), ($^3$H)-diprenorphine (µ agonist), [$^3$H]-bremacozine (κ agonist), [$^3$H]-dihydromorphine (µ agonist), ($^3$H)-ethylketocyclazocine (κ agonist) or ($^{125}$I)-β-endorphin. Although low levels of specific binding were seen using ($^3$H-naloxone (µ antagonist), the significance of these results was compromised by the fact that untransfected COS-7 and Ltk⁻ cells also showed endogenous low levels of specific ($^3$H)-naloxone binding.

Figure 4A:
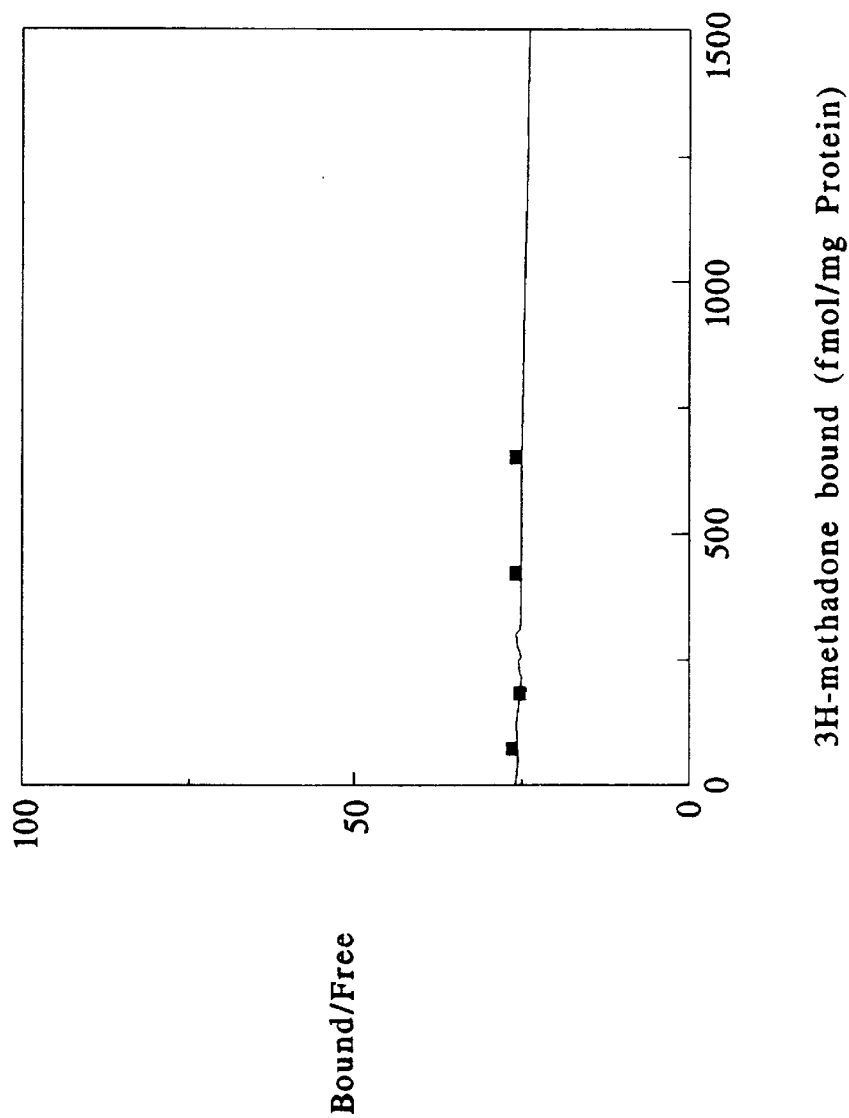
FIGS. 4A and 4B present affinity binding experiment results of $^3$H-methadone binding to COS-7 cells (FIG. 4A) and to COS-7 cells expressing the methadone-specific mammalian opioid receptor of the invention (FIG. 4B).
Figure 4B:
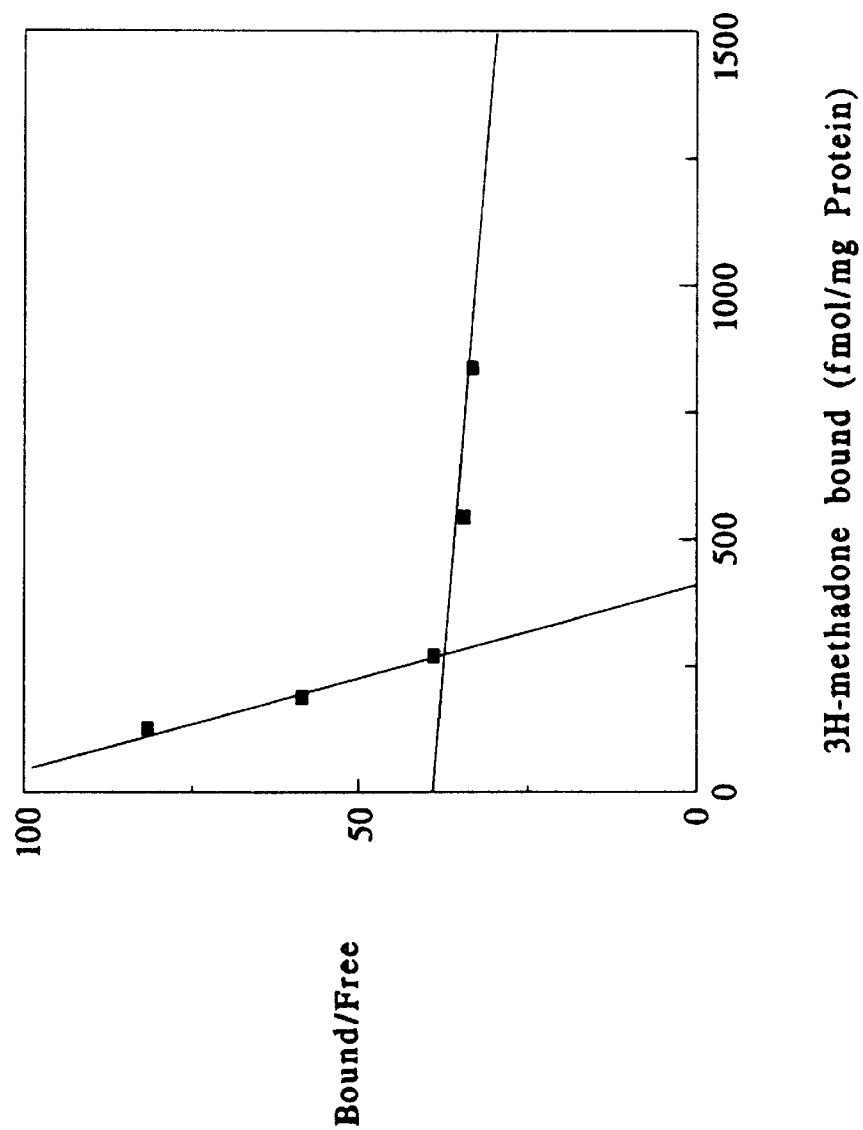

Surprisingly, however, specific binding was found using ($^3$H)-methadone. The results of Scatchard analysis of the methadone binding data are shown in FIGS. 4A and 4B. For Scatchard analysis experiments, 0.25 ml aliquots of crude plasma membrane homogenate from transfected cell cultures was incubated in duplicate with increasing concentrations of ($^3$H)methadone (70.3 Ci/mmol; 10–3000 pM final concentration) under conditions described above. The estimated value for $B_{max}$ was derived from these data were obtained using the LIGAND computer program. FIG. 4A shows the results of radiolabeled methadone binding with untransfected COS-7 cells; similar results were found with Ltk⁻ cell membranes. These results demonstrate no or negligible amounts of endogenous methadone binding by these cell membranes. FIG. 4B shows the results using COS-7 cells transfected with the RcRSV-LC132 expression construct.

The levels of specific binding shown in this graph correspond to a dissociation constant ($K_D$) of about $10^{-10}$M for methadone and a $B_{max}$ of about 400–450 femtomoles/µg protein for the novel mammalian opioid receptor expressed by these cells.

Thus, the novel mammalian opioid receptor disclosed herein has the heretofore unknown property of exhibiting specific binding to the opiate analog, methadone, while showing no specific binding to a variety of other known opioid receptor agonists and antagonists. These results support the conclusion that the receptor disclosed herein is a completely novel and heretofore unsuspected member of the opioid receptor family, termed herein therefore MSOR.

EXAMPLE 4

Brain Tissue Distribution of Methadone-Specific Opioid Receptor Expression

The distribution of mRNA corresponding to expression of the MSOR receptor gene in various regions of the rat brain was determined by in situ hybridization of rat brain slices. Rat brain sections were made and were hybridized with an ($^{35}$S)-CTP-labeled synthetic RNA (termed a riboprobe; see Promega Biotech Riboprobe System, Madison, Wis.) using conventional techniques.

In situ hybridization of rat brain section was performed as follows. Male Sprague-Dawley rats (200 g) were anesthetized and perfused at 40° C. with 1 L of 4% paraformaldehyde in borate buffer, pH 9.5 (fixation buffer). Brains were dissected and incubated in fixation buffer for 8 h, then further incubated overnight in fixation buffer containing 10% sucrose. Brains were then sectioned serially into series of 15µm slices with a sliding microtome. Sections were prepared and hybridized as described in Arriza et al., 1988, Neuron 1: 887–900. A 600 bp fragment of the MSOR cDNA was subcloned into a pBKS vector (Stratagene) and used to synthesize a ($^{35}$S)-CTP radiolabeled antisense cRNA probe (see Sambrook et al., ibid.) Sections were hybridized at 65° C. for 24 h with $^{35}$S-labeled probe (~1×10$^7$ cpm/ml) in 65% formamide, 0.26M NaCl, 1.3X Denhardt's solution, 13 mM Tris (pH 8.0), 1.3 mM EDTA and 13% dextran sulfate. Slides were washed in 4×SSC (0.6M NaCl, 0.06M Na citrate), digested with RNase (20 pg/ml) for 30 min at 37° C.), and then rinsed to a final stringency of 0.1X SSC at 65° C. for 30 min. Sections were dehydrated, dipped in NTB-2 emulsion, and developed after 21 days.

Figure 3B:
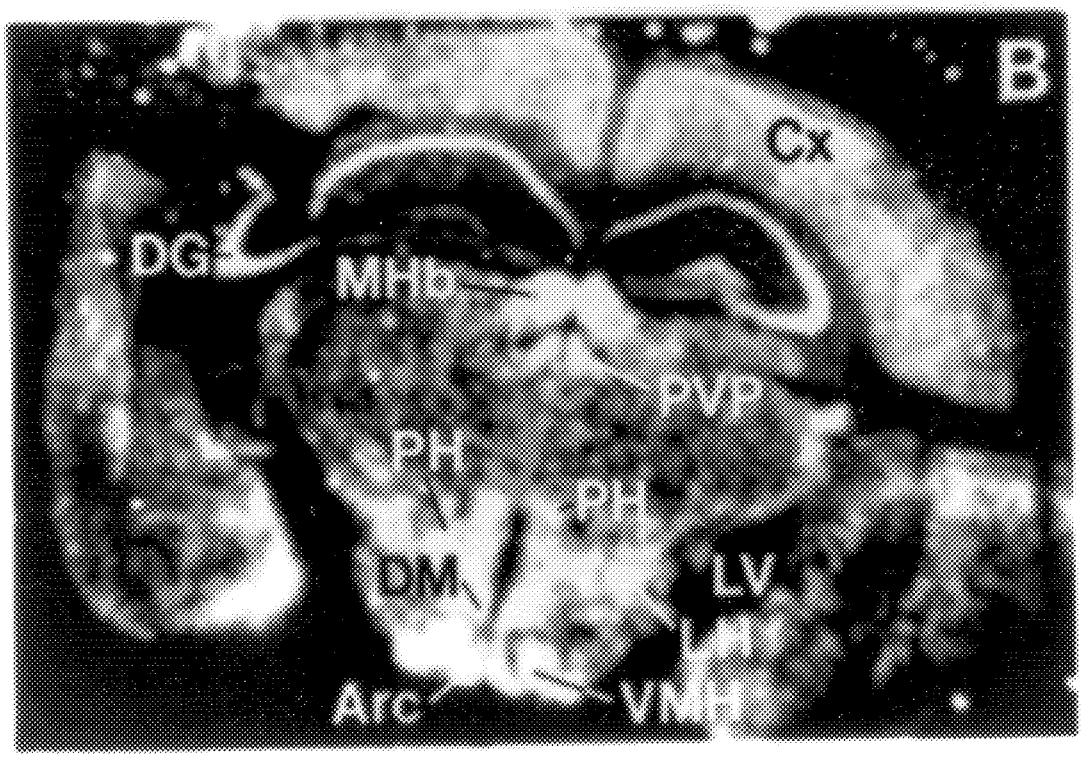
Figure 3C:
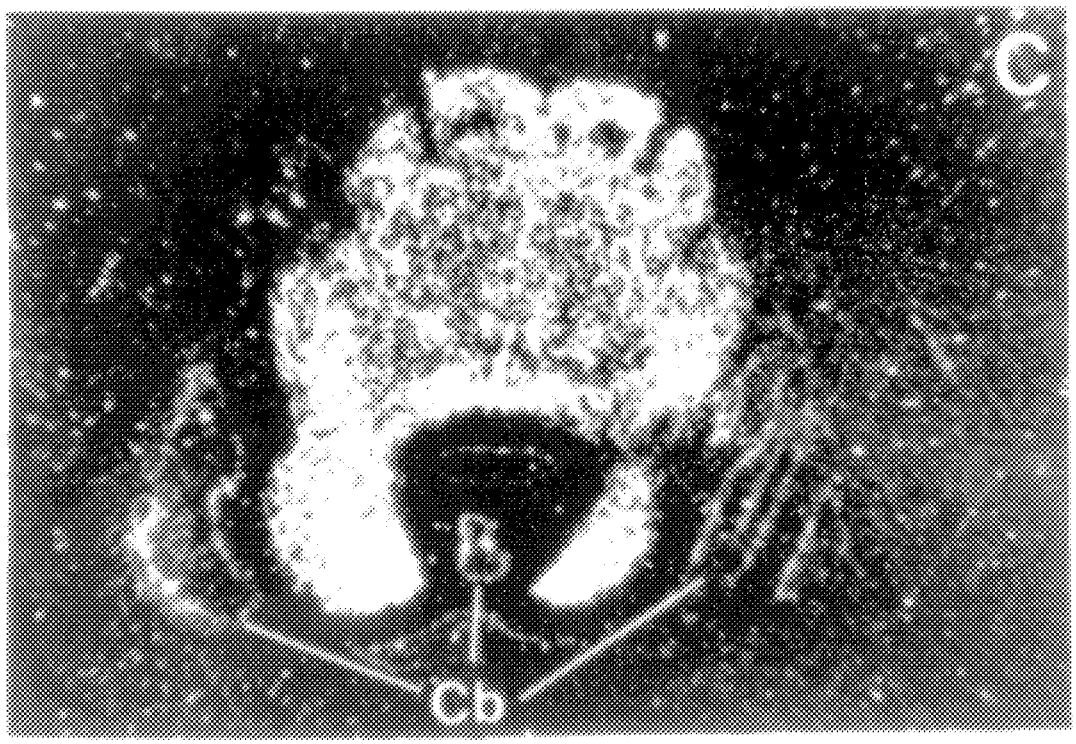

Results of these experiments are shown in FIGS. 3A through 3C. FIG. 3A shows a section through the frontal cortex, preoptic area and caudate putamen; FIG. 3B shows a section through the hypothalamus, thalamus and hippocampus; and FIG. 3C shows a section through the pons and cerebellum. These experiments localized high level MSOR expression in the hypothalamus (arcuate (Arc), posterior (PH), lateral (LH) and ventromedial (VMH) hypothalamic nuclei, FIG.3B), certain nuclei of the thalamus (paraventricular thalamic nuclei (PVP), FIG. 3B), the medial habenula (MHb, FIG. 3B), the CA regions of the hypothalamus, the dentate gyrus (DG, FIG. 3B), the locus coeruleus and certain cortical areas (medial preoptic are (MPA), FIG. 3A and the cortex (Cx), FIG. 3B). Virtually no signal was seen in the caudate putamen (Cpu, FIG. 3A) or cerebellum (Cb, FIG. 3C). Strong hybridization was also detected in sections of the brainstem (FIG. 3C) and the spinal cord (not shown).

These results demonstrate that the MSOR receptor disclosed herein is expressed in rat brain in a variety of anatomically-distinct sites, suggesting an important role for this receptor in both higher brain function and central nervous system control of motor and sensory nerve signalling.

EXAMPLE 5

Construction of Vaccinia Virus-Recombinant Expression Constructs for Functional Expression of the MSOR Opioid Receptor Using an alternative approach, the MSOR opioid receptor protein of the invention is expressed in human HeLa (vulval adenocarcinoma) cells via a vaccinia virus-based construct. In these experiments, the MSOR receptor cDNA of the invention is excised from the RcRSV construct and subcloned into a modified pBluescript (Strategene) vector wherein the MSOR receptor cDNA is under the control of a bacteriophage T7 RNA polymerase promoter (as is described in Blakely et al., 1991, Anal. Biochem. 194: 302–308). HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with the MSOR receptor construct described above using a lipofectin-mediated (Bethesda Research Labs, Gaithersburg, Md.) transfection protocol (see Felgner et al., 1987, Proc. Nati. Acad. Sci. USA 84: 7413–7417). Cells are then incubated for 12–24 h before being assayed for MSOR receptor expression by functional assays or Northern hybridization assays.

EXAMPLE 6

Construction of Fusion Proteins-Recombinant Expression Constructs for Expression of Immunologically-Active Epitopes of the MSOR Opioid Receptor The MSOR opioid receptor protein of the invention are expressed as fusion proteins in bacteria to produce immunologically-active epitopes. In these experiments, the MSOR opioid receptor cDNA of the invention is excised from the RcRSV construct and subcloned into a pGEX-2T construct (Pharmacia, Piscataway, N.J.) whereby the coding sequences of the MSOR receptor cDNA is translationally in-frame with sequences encoding glutathione-S-transferase (described in Arriza et al., 1992, J. Neurosci. 12: 4045–4055), or any other protein construct for which a preparative isolation method is available. After introduction of the fusion construct into bacterial cells (*E. coli*, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against the MSOR opioid receptor of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual,* Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

|  | TMI | TMII | TMIII | TMIV | TMV | TMVI | TMVII | TM avg | avg/all |
|---|---|---|---|---|---|---|---|---|---|
| LC132[a] vs rat $\mu$[a] | 58[b] | 67 | 77 | 48 | 67 | 59 | 85 | 66 | 48 |
| LC132 vs rat $\kappa$[c] | 35 | 67 | 82 | 43 | 71 | 73 | 80 | 64 | 47 |
| LC132 vs mouse $\delta$[d] | 46 | 67 | 77 | 52 | 63 | 59 | 75 | 63 | 46 |
| rat $\kappa$ vs mouse $\delta$ | 62 | 83 | 91 | 57 | 75 | 64 | 90 | 75 | 52 |
| rat $\mu$ vs mouse $\delta$ | 69 | 90 | 86 | 48 | 83 | 77 | 85 | 77 | 51 |
| rat $\mu$ vs rat $\kappa$ | 54 | 80 | 91 | 33 | 75 | 73 | 95 | 72 | 49 |

[a]Bunzow et al.
[b]percent
[c]Minami et al. (1993) FEBS Letters 329, 291.
[d]Evans et al. (1992) Science 258, 1952.

---

What we claim is:

1. A method of screening a compound for binding to a mammalian methadone-specific opioid receptor, the method comprising the steps of:
   (a) transforming a host cell with a recombinant expression construct comprising a nucleic acid encoding a mammalian methadone-specific opioid receptor having an amino acid sequence identified as Seq. ID No. 4;
   (b) culturing the host cell under conditions wherein the host cell expresses the mammalian methadone-specific opioid receptor; and
   (c) assaying the transformed host cell with the compound to determine whether the compound binds to the mammalian methadone-specific opioid receptor.

2. The method of claim 1 wherein the compound is a naturally-occurring, endogenous opioid-like compound from a mammal.

3. A method of screening a compound for competitive binding to a mammalian methadone-specific opioid receptor, the method comprising the following steps:
   (a) transforming a host cell with a recombinant expression construct comprising a nucleic acid encoding a mammalian methadone-specific opioid receptor having an amino acid sequence identified as Seq. ID No. 4;
   (b) culturing the host cell under conditions wherein the host cell expresses the mammalian methadone-specific opioid receptor;
   (c) assaying the transformed cell with the compound in the presence and in the absence of a naturally-occurring or synthetic agonist or antagonist of the mammalian methadone-specific opioid receptor; and
   (d) determining whether the compound competes with the agonist or antagonist for binding to the receptor.

4. The method of claim 3, wherein the compound is detectably-labeled.

5. The method of claim 3, wherein the mammalian methadone-specific opioid receptor agonist or antagonist is detectably-labeled.

6. The method of claim 3, wherein competitive binding of the compound to the mammalian methadone-specific opioid receptor is quantitatively measured by assaying the transformed host cell with varying amounts of the compound in the presence of a detectably-labeled mammalian methadone-specific opioid receptor agonist or antagonist.

7. A method of screening to determine if a compound is an inhibitor of a mammalian methadone-specific opioid receptor, the method comprising the following steps:
   (a) transforming a host cell with a recombinant expression construct comprising a nucleic acid encoding a mammalian methadone-specific opioid receptor having an amino acid sequence identified as Seq. ID No. 4;
   (b) culturing the host cell under conditions wherein the host cell expresses the mammalian methadone-specific opioid receptor;
   (c) contacting the transformed host cell with the compound in the presence of methadone; and
   (d) determining whether the compound is capable of inhibiting methadone binding to the mammalian methadone-specific opioid receptor.

8. The method of claim 7, wherein the compound is detectably-labeled.

9. The method of claim 7, wherein methadone is detectably-labeled.

10. The method of claim 7, wherein inhibition of the mammalian methadone-specific opioid receptor by the compound is quantitatively measured by assaying the transformed host cell with varying amounts of the compound in the presence of detectably-labeled methadone.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATGAATTCAC NRTSATGAGY GTSGACHGHT A        3 1

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTGTCGACRT ARRAGRAYNG GRTT        2 4

(2) INFORMATION FOR SEQ ID NO:3:

(i) SEQUENCE CHARACTERISTICS:
        (A) LENGTH: 1452 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..181

(ix) FEATURE:
        (A) NAME/KEY: CDS
        (B) LOCATION: 182..1282

(ix) FEATURE:
        (A) NAME/KEY: 3'UTR
        (B) LOCATION: 1283..1452

(xi) SEQUENCE DESCRIPTION: SEQ ID NO:3:

```
CCGAGGAGCC ATTCCCAGCC GCAGCAGACC CCAATCTAGA GTGAGAGTCA TTGCTCAGTC          60

CACTGTGCTC CTGCCTGCCC GCCTTTCTGC TAAGCATTGG GGTCTATTTT GCGCCCAGCT         120

TCTGAAGAGG CTGTGTGTGC CGTTGGAGGA ACTGTACTGA GTGGCTTTGC AGGGTGACAG         180

C ATG GAG TCC CTC TTT CCT GCT CCA TAC TGG GAG GTC TTG CAT GGC            226
  Met Glu Ser Leu Phe Pro Ala Pro Tyr Trp Glu Val Leu His Gly
   1               5                  10                  15

AGC CAC TTT CAA GGG AAC CTG TCC CTC CTA AAT GAG ACC GTA CCC CAC          274
Ser His Phe Gln Gly Asn Leu Ser Leu Leu Asn Glu Thr Val Pro His
                 20                  25                  30

CAC CTG CTC CTC AAT GCT AGT CAC AGC GCC TTC CTG CCC CTT GGA CTC          322
His Leu Leu Leu Asn Ala Ser His Ser Ala Phe Leu Pro Leu Gly Leu
             35                  40                  45

AAG GTC ACC ATC GTG GGG CTC ATC TTG GCT GTG TGC ATC GGG GGG CTC          370
Lys Val Thr Ile Val Gly Leu Ile Leu Ala Val Cys Ile Gly Gly Leu
         50                  55                  60

CTG GGG AAC TGC CTC GTC ATG TAT GTC ATC CTC AGG ACA CCC AAG ATG          418
Leu Gly Asn Cys Leu Val Met Tyr Val Ile Leu Arg Thr Pro Lys Met
     65                  70                  75

AAG ACA GCT ACC AAC ATT TAC ATA TTT AAT CTG GCA CTG GCT GAT ACC          466
Lys Thr Ala Thr Asn Ile Tyr Ile Phe Asn Leu Ala Leu Ala Asp Thr
 80                  85                  90                  95

CTG GTC TTG CTA ACA CTG CCC TTC CAG GGC ACA GAC ATC CTA CTG GGC          514
Leu Val Leu Leu Thr Leu Pro Phe Gln Gly Thr Asp Ile Leu Leu Gly
                 100                 105                 110

TTC TGG CCA TTT GGG AAA GCA CTC TGC AAG ACT GTC ATT GCT ATC GAC          562
Phe Trp Pro Phe Gly Lys Ala Leu Cys Lys Thr Val Ile Ala Ile Asp
             115                 120                 125

TAC TAC AAC ATG TTT ACC AGC ACT TTT ACT CTG ACC GCC ATG AGC GTA          610
Tyr Tyr Asn Met Phe Thr Ser Thr Phe Thr Leu Thr Ala Met Ser Val
         130                 135                 140

GAC CGC TAT GTG GCT ATC TGC CAC CCT ATC CGT GCC CTT GAT GTT CGG          658
Asp Arg Tyr Val Ala Ile Cys His Pro Ile Arg Ala Leu Asp Val Arg
     145                 150                 155

ACA TCC AGC AAA GCC CAG GCT GTT AAT GTG GCC ATA TGG GCC CTG GCT          706
Thr Ser Ser Lys Ala Gln Ala Val Asn Val Ala Ile Trp Ala Leu Ala
 160                 165                 170                 175

TCA GTG GTT GGT GTT CCT GTT GCC ATC ATG GGT TCA GCA CAA GTG GAA          754
Ser Val Val Gly Val Pro Val Ala Ile Met Gly Ser Ala Gln Val Glu
                 180                 185                 190
```

| | | | | | | | | | | | | | | | | |
|---|---|---|---|---|---|---|---|---|---|---|---|---|---|---|---|---|
| GAT | GAA | GAG | ATC | GAG | TGC | CTG | GTG | GAG | ATC | CCT | GCC | CCT | CAG | GAC | TAT | 802 |
| Asp | Glu | Glu | Ile 195 | Glu | Cys | Leu | Val | Glu 200 | Ile | Pro | Ala | Pro | Gln 205 | Asp | Tyr | |
| TGG | GGC | CCT | GTA | TTC | GCC | ATC | TGC | ATC | TTC | CTT | TTT | TCC | TTC | ATC | ATC | 850 |
| Trp | Gly | Pro 210 | Val | Phe | Ala | Ile | Cys 215 | Ile | Phe | Leu | Phe | Ser 220 | Phe | Ile | Ile | |
| CCT | GTG | CTG | ATC | ATC | TCT | GTC | TGC | TAC | AGC | CTC | ATG | ATT | CGA | CGA | CTT | 898 |
| Pro | Val 225 | Leu | Ile | Ile | Ser | Val 230 | Cys | Tyr | Ser | Leu | Met 235 | Ile | Arg | Arg | Leu | |
| CGT | GGT | GTC | CGT | CTG | CTT | TCA | GGC | TCC | CGG | GAG | AAG | GAC | CGA | AAC | CTG | 946 |
| Arg 240 | Gly | Val | Arg | Leu | Leu 245 | Ser | Gly | Ser | Arg | Glu 250 | Lys | Asp | Arg | Asn | Leu 255 | |
| CGG | CGT | ATC | ACT | CGA | CTG | GTG | CTG | GTA | GTG | GTG | GCT | GTG | TTT | GTG | GGC | 994 |
| Arg | Arg | Ile | Thr | Arg 260 | Leu | Val | Leu | Val | Val 265 | Val | Ala | Val | Phe | Val 270 | Gly | |
| TGC | TGG | ACG | CCT | GTG | CAG | GTG | TTT | GTC | CTG | GTT | CAA | GGA | CTG | GGT | GTT | 1042 |
| Cys | Trp | Thr | Pro 275 | Val | Gln | Val | Phe | Val 280 | Leu | Val | Gln | Gly | Leu 285 | Gly | Val | |
| CAG | CCA | GGT | AGT | GAG | ACT | GCA | GTT | GCC | ATC | CTG | CGC | TTC | TGC | ACA | GCC | 1090 |
| Gln | Pro | Gly 290 | Ser | Glu | Thr | Ala | Val 295 | Ala | Ile | Leu | Arg | Phe 300 | Cys | Thr | Ala | |
| CTG | GGC | TAT | GTC | AAC | AGT | TGT | CTC | AAT | CCC | ATT | CTC | TAT | GCT | TTC | CTG | 1138 |
| Leu | Gly 305 | Tyr | Val | Asn | Ser | Cys 310 | Leu | Asn | Pro | Ile | Leu 315 | Tyr | Ala | Phe | Leu | |
| GAT | GAG | AAC | TTC | AAG | GCC | TGC | TTT | AGA | AAG | TTC | TGC | TGT | GCT | TCA | TCC | 1186 |
| Asp 320 | Glu | Asn | Phe | Lys | Ala 325 | Cys | Phe | Arg | Lys | Phe 330 | Cys | Cys | Ala | Ser | Ser 335 | |
| CTG | CAC | CGG | GAG | ATG | CAG | GTT | TCT | GAT | CGT | GTG | CGG | ACG | ATT | GCC | AAG | 1234 |
| Leu | His | Arg | Glu | Met 340 | Gln | Val | Ser | Asp | Arg 345 | Val | Arg | Thr | Ile | Ala 350 | Lys | |
| GAT | GTT | GGC | CTT | GGT | TGC | AAG | ACT | TCT | GAG | ACA | GTA | CCA | CGG | CCA | GCA | 1282 |
| Asp | Val | Gly | Leu 355 | Gly | Cys | Lys | Thr | Ser 360 | Glu | Thr | Val | Pro | Arg 365 | Pro | Ala | |

| | | | | |
|---|---|---|---|---|
| TGACTAGGCG | TGGACCTGCC | CATGGTGCCT | GTCAGCCAC | AGAGCCCATC CTACACCCAA | 1342 |
| CACGGAGCTC | ACACAGGTCA | CTGCTCTCTA | GGTTGACCCT | GAACCTTGAG CATCTGGAGC | 1402 |
| CTTGAATGGC | TTTTCTTTTG | GATCAGGATG | CTCAGTCCTA | GAGGAAGACC | 1452 |

( 2 ) INFORMATION FOR SEQ ID NO:4:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Glu | Ser | Leu | Phe 5 | Pro | Ala | Pro | Tyr | Trp 10 | Glu | Val | Leu | His | Gly 15 | Ser |
| His | Phe | Gln | Gly 20 | Asn | Leu | Ser | Leu | Leu 25 | Asn | Glu | Thr | Val | Pro 30 | His | His |
| Leu | Leu | Leu 35 | Asn | Ala | Ser | His | Ser 40 | Ala | Phe | Leu | Pro | Leu 45 | Gly | Leu | Lys |
| Val | Thr 50 | Ile | Val | Gly | Leu | Ile 55 | Leu | Ala | Val | Cys | Ile 60 | Gly | Gly | Leu | Leu |
| Gly 65 | Asn | Cys | Leu | Val | Met 70 | Tyr | Val | Ile | Leu | Arg 75 | Thr | Pro | Lys | Met | Lys 80 |
| Thr | Ala | Thr | Asn | Ile 85 | Tyr | Ile | Phe | Asn | Leu 90 | Ala | Leu | Ala | Asp | Thr 95 | Leu |

| Val | Leu | Leu | Thr | Leu | Pro | Phe | Gln | Gly | Thr | Asp | Ile | Leu | Leu | Gly | Phe |
|---|---|---|---|---|---|---|---|---|---|---|---|---|---|---|---|
| | | | 100 | | | | 105 | | | | | 110 | | | |
| Trp | Pro | Phe | Gly | Lys | Ala | Leu | Cys | Lys | Thr | Val | Ile | Ala | Ile | Asp | Tyr |
| | | | 115 | | | | 120 | | | | | 125 | | | |
| Tyr | Asn | Met | Phe | Thr | Ser | Thr | Phe | Thr | Leu | Thr | Ala | Met | Ser | Val | Asp |
| | | 130 | | | | 135 | | | | | 140 | | | | |
| Arg | Tyr | Val | Ala | Ile | Cys | His | Pro | Ile | Arg | Ala | Leu | Asp | Val | Arg | Thr |
| 145 | | | | | 150 | | | | | 155 | | | | | 160 |
| Ser | Ser | Lys | Ala | Gln | Ala | Val | Asn | Val | Ala | Ile | Trp | Ala | Leu | Ala | Ser |
| | | | | 165 | | | | | 170 | | | | | 175 | |
| Val | Val | Gly | Val | Pro | Val | Ala | Ile | Met | Gly | Ser | Ala | Gln | Val | Glu | Asp |
| | | | | 180 | | | | 185 | | | | | 190 | | |
| Glu | Glu | Ile | Glu | Cys | Leu | Val | Glu | Ile | Pro | Ala | Pro | Gln | Asp | Tyr | Trp |
| | | 195 | | | | 200 | | | | | 205 | | | | |
| Gly | Pro | Val | Phe | Ala | Ile | Cys | Ile | Phe | Leu | Phe | Ser | Phe | Ile | Ile | Pro |
| | 210 | | | | | 215 | | | | | 220 | | | | |
| Val | Leu | Ile | Ile | Ser | Val | Cys | Tyr | Ser | Leu | Met | Ile | Arg | Arg | Leu | Arg |
| 225 | | | | | 230 | | | | | 235 | | | | | 240 |
| Gly | Val | Arg | Leu | Leu | Ser | Gly | Ser | Arg | Glu | Lys | Asp | Arg | Asn | Leu | Arg |
| | | | | 245 | | | | | 250 | | | | | 255 | |
| Arg | Ile | Thr | Arg | Leu | Val | Leu | Val | Val | Ala | Val | Phe | Val | Gly | Cys |
| | | | 260 | | | | | 265 | | | | | 270 | | |
| Trp | Thr | Pro | Val | Gln | Val | Phe | Val | Leu | Val | Gln | Gly | Leu | Gly | Val | Gln |
| | | 275 | | | | | 280 | | | | | 285 | | | |
| Pro | Gly | Ser | Glu | Thr | Ala | Val | Ala | Ile | Leu | Arg | Phe | Cys | Thr | Ala | Leu |
| | 290 | | | | | 295 | | | | | 300 | | | | |
| Gly | Tyr | Val | Asn | Ser | Cys | Leu | Asn | Pro | Ile | Leu | Tyr | Ala | Phe | Leu | Asp |
| 305 | | | | | 310 | | | | | 315 | | | | | 320 |
| Glu | Asn | Phe | Lys | Ala | Cys | Phe | Arg | Lys | Phe | Cys | Cys | Ala | Ser | Ser | Leu |
| | | | | 325 | | | | | 330 | | | | | 335 | |
| His | Arg | Glu | Met | Gln | Val | Ser | Asp | Arg | Val | Arg | Thr | Ile | Ala | Lys | Asp |
| | | | 340 | | | | | 345 | | | | | 350 | | |
| Val | Gly | Leu | Gly | Cys | Lys | Thr | Ser | Glu | Thr | Val | Pro | Arg | Pro | Ala | |
| | | 355 | | | | | 360 | | | | | 365 | | | |

( 2 ) INFORMATION FOR SEQ ID NO:5:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..398
        ( D ) OTHER INFORMATION: /label=Identifier
           / note= "Rat Mu-Opioid Receptor"

( x i ) SEQUENCE DESCRIPTION: SEQ ID NO:5:

| Met | Asp | Ser | Ser | Thr | Gly | Pro | Gly | Asn | Thr | Ser | Asp | Cys | Ser | Asp | Pro |
|---|---|---|---|---|---|---|---|---|---|---|---|---|---|---|---|
| 1 | | | | 5 | | | | | 10 | | | | | 15 | |
| Leu | Ala | Gln | Ala | Ser | Cys | Ser | Pro | Ala | Pro | Gly | Ser | Trp | Leu | Asn | Leu |
| | | | | 20 | | | | | 25 | | | | | 30 | |
| Ser | His | Val | Asp | Gly | Asn | Gln | Ser | Asp | Pro | Cys | Gly | Leu | Asn | Arg | Thr |
| | | | 35 | | | | | 40 | | | | | 45 | | |
| Gly | Leu | Gly | Gly | Asn | Asp | Ser | Leu | Cys | Pro | Gln | Thr | Gly | Ser | Pro | Ser |
| | 50 | | | | | 55 | | | | | 60 | | | | |

Met Val Thr Ala Ile Thr Ile Met Ala Leu Tyr Ser Ile Val Cys Val
65               70              75              80

Val Gly Leu Phe Gly Asn Phe Leu Val Met Tyr Val Ile Val Arg Tyr
            85              90              95

Thr Lys Met Lys Thr Ala Thr Asn Ile Tyr Ile Phe Asn Leu Ala Leu
            100             105             110

Ala Asp Ala Leu Ala Thr Ser Thr Leu Pro Phe Gln Ser Val Asn Tyr
        115             120             125

Leu Met Gly Thr Trp Pro Phe Gly Thr Ile Leu Cys Lys Ile Val Ile
    130             135             140

Ser Ile Asp Tyr Tyr Asn Met Phe Thr Ser Ile Phe Thr Leu Cys Thr
145             150             155             160

Met Ser Val Asp Arg Tyr Ile Ala Val Cys His Pro Val Lys Ala Leu
            165             170             175

Asp Phe Arg Thr Pro Arg Asn Ala Lys Ile Val Asn Val Cys Asn Trp
            180             185             190

Ile Leu Ser Ser Ala Ile Gly Leu Pro Val Met Phe Met Ala Thr Thr
        195             200             205

Lys Tyr Arg Gln Gly Ser Ile Asp Cys Thr Leu Thr Phe Ser His Pro
    210             215             220

Thr Trp Tyr Trp Glu Asn Leu Leu Lys Ile Cys Val Phe Ile Phe Ala
225             230             235             240

Phe Ile Met Pro Ile Leu Ile Ile Thr Val Cys Tyr Gly Leu Met Ile
            245             250             255

Leu Arg Leu Lys Ser Val Arg Met Leu Ser Gly Ser Lys Glu Lys Asp
            260             265             270

Arg Asn Leu Arg Arg Ile Thr Arg Met Val Leu Val Val Val Ala Val
        275             280             285

Phe Ile Val Cys Trp Thr Pro Ile His Ile Tyr Val Ile Ile Lys Ala
    290             295             300

Leu Ile Thr Ile Pro Glu Thr Thr Phe Gln Thr Val Ser Trp His Phe
305             310             315             320

Cys Ile Ala Leu Gly Tyr Thr Asn Ser Cys Leu Asn Pro Val Leu Tyr
            325             330             335

Ala Phe Leu Asp Glu Asn Phe Lys Arg Cys Phe Arg Glu Phe Cys Ile
        340             345             350

Pro Thr Ser Ser Thr Ile Glu Gln Gln Asn Ser Thr Arg Val Arg Gln
        355             360             365

Asn Thr Arg Glu His Pro Ser Thr Ala Asn Thr Val Asp Arg Thr Asn
    370             375             380

His Gln Leu Glu Asn Leu Glu Ala Glu Thr Ala Pro Leu Pro
385             390             395

( 2 ) INFORMATION FOR SEQ ID NO:6:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..372
        ( D ) OTHER INFORMATION: /label=Identifier
           / note= "Mouse Delta-Opioid Receptor"

( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Glu | Leu | Val | Pro<br>5 | Ser | Ala | Arg | Ala | Glu<br>10 | Leu | Gln | Ser | Ser | Pro<br>15 | Leu |
| Val | Asn | Leu | Ser<br>20 | Asp | Ala | Phe | Pro<br>25 | Ser | Ala | Phe | Pro | Ser<br>30 | Ala | Gly | Ala |
| Asn | Ala | Ser<br>35 | Gly | Ser | Pro | Gly | Ala<br>40 | Arg | Ser | Ala | Ser | Ser<br>45 | Leu | Ala | Leu |
| Ala | Ile<br>50 | Ala | Ile | Thr | Ala | Leu<br>55 | Tyr | Ser | Ala | Val | Cys<br>60 | Ala | Val | Gly | Leu |
| Ile<br>65 | Gly | Asn | Val | Leu | Val<br>70 | Met | Leu | Gly | Ile | Val<br>75 | Arg | Tyr | Thr | Lys | Leu<br>80 |
| Lys | Thr | Ala | Thr | Asn<br>85 | Ile | Tyr | Ile | Phe | Asn<br>90 | Leu | Ala | Leu | Ala | Asp<br>95 | Ala |
| Leu | Ala | Thr | Ser<br>100 | Thr | Leu | Pro | Phe | Gln<br>105 | Ser | Ala | Lys | Tyr | Leu<br>110 | Met | Glu |
| Thr | Trp | Pro<br>115 | Phe | Gly | Glu | Leu | Leu<br>120 | Cys | Lys | Ala | Val | Leu<br>125 | Ser | Ile | Asp |
| Tyr | Tyr<br>130 | Asn | Met | Phe | Thr | Ser<br>135 | Ile | Phe | Thr | Leu | Thr<br>140 | Met | Met | Ser | Val |
| Asp<br>145 | Arg | Tyr | Ile | Ala | Val<br>150 | Cys | His | Pro | Val | Lys<br>155 | Ala | Leu | Asp | Phe | Arg<br>160 |
| Thr | Pro | Ala | Lys | Ala<br>165 | Lys | Leu | Ile | Asn | Ile<br>170 | Cys | Ile | Trp | Val | Leu<br>175 | Ala |
| Ser | Gly | Val | Gly<br>180 | Val | Pro | Ile | Met | Val<br>185 | Met | Ala | Val | Thr | Gln<br>190 | Pro | Arg |
| Asp | Phe | Ala<br>195 | Val | Val | Cys | Met | Leu<br>200 | Gln | Phe | Pro | Ser | Pro<br>205 | Ser | Trp | Tyr |
| Trp | Asp<br>210 | Thr | Val | Thr | Lys | Ile<br>215 | Cys | Val | Phe | Ile | Phe<br>220 | Ala | Phe | Val | Val |
| Pro<br>225 | Ile | Leu | Ile | Ile | Thr<br>230 | Val | Cys | Tyr | Gly | Leu<br>235 | Met | Leu | Leu | Arg | Leu<br>240 |
| Arg | Ser | Val | Arg | Leu<br>245 | Leu | Ser | Gly | Ser | Lys<br>250 | Glu | Lys | Asp | Arg | Ser<br>255 | Leu |
| Arg | Arg | Ile | Thr<br>260 | Arg | Met | Val | Leu | Val<br>265 | Val | Val | Gly | Ala | Phe<br>270 | Val | Val |
| Cys | Trp | Ala<br>275 | Pro | Ile | His | Ile | Phe<br>280 | Val | Ile | Val | Trp | Thr<br>285 | Leu | Val | Asp |
| Ile | Asn<br>290 | Arg | Arg | Asp | Pro | Leu<br>295 | Val | Val | Ala | Ala | Leu<br>300 | His | Leu | Cys | Ile |
| Ala<br>305 | Leu | Gly | Tyr | Ala | Asn<br>310 | Ser | Ser | Leu | Asn | Pro<br>315 | Val | Leu | Tyr | Ala | Phe<br>320 |
| Leu | Asp | Glu | Asn | Phe<br>325 | Lys | Arg | Cys | Phe | Arg<br>330 | Gln | Leu | Cys | Arg | Thr<br>335 | Pro |
| Cys | Gly | Arg | Gln<br>340 | Glu | Pro | Gly | Ser | Leu<br>345 | Arg | Arg | Pro | Arg | Gln<br>350 | Ala | Thr |
| Thr | Arg | Glu<br>355 | Arg | Val | Thr | Ala | Cys<br>360 | Thr | Pro | Ser | Asp | Gly<br>365 | Pro | Gly | Gly |
| Gly | Ala | Ala<br>370 | Ala | | | | | | | | | | | | |

( 2 ) INFORMATION FOR SEQ ID NO:7:

( i ) SEQUENCE CHARACTERISTICS:
    ( A ) LENGTH: 380 amino acids
    ( B ) TYPE: amino acid (D) TOPOLOGY: linear (ii) MOLECULE TYPE: protein (ix) FEATURE:
    (A) NAME/KEY: Protein
    (B) LOCATION: 1..380
    (D) OTHER INFORMATION: /label=Identifier
        / note= "Mouse Kappa-Opioid Receptor"

(xi) SEQUENCE DESCRIPTION: SEQ ID NO:7:

```
Met Glu Ser Pro Ile Gln Ile Phe Arg Gly Asp Pro Gly Pro Thr Cys
 1               5                   10                  15

Ser Pro Ser Ala Cys Leu Leu Pro Asn Ser Ser Ser Trp Phe Pro Asn
            20                  25                  30

Trp Ala Glu Ser Asp Ser Asn Gly Ser Val Gly Ser Glu Asp Gln Gln
        35                  40                  45

Leu Glu Ser Ala His Ile Ser Pro Ala Ile Pro Val Ile Ile Thr Ala
     50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Ala Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
    130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ala Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Glu Tyr Ser Trp Trp Asp Leu
    210                 215                 220

Phe Met Lys Ile Cys Val Phe Val Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270

Thr Lys Leu Val Leu Val Val Ala Val Phe Ile Ile Cys Trp Thr
        275                 280                 285

Pro Ile His Ile Phe Ile Leu Val Glu Ala Leu Gly Ser Thr Ser His
    290                 295                 300

Ser Thr Ala Ala Leu Ser Ser Tyr Tyr Phe Cys Ala Ile Leu Gly Tyr
305                 310                 315                 320

Thr Asn Ser Ser Leu Asn Pro Val Leu Tyr Ala Phe Leu Asp Glu Asn
                325                 330                 335

Phe Lys Arg Cys Phe Arg Asp Phe Cys Phe Pro Ile Lys Met Arg Met
            340                 345                 350

Glu Arg Gln Ser Thr Asn Arg Val Arg Asn Thr Val Gln Asp Pro Ala
        355                 360                 365
```

```
Ser  Met  Arg  Asp  Val  Gly  Gly  Met  Asn  Lys  Pro  Val
     370                 375                      380
```